(12) United States Patent
Cantrell et al.

(10) Patent No.: US 11,497,412 B2
(45) Date of Patent: Nov. 15, 2022

(54) COMBINED OXYGEN UTILIZATION, STRAIN, AND ANATOMIC IMAGING WITH MAGNETIC RESONANCE IMAGING

(71) Applicant: The University of Chicago, Chicago, IL (US)

(72) Inventors: Charles G. Cantrell, Burnsville, MN (US); Keigo Kawaji, Chicago, IL (US); Amit R. Patel, Chicago, IL (US); Timothy J. Carroll, Chicago, IL (US)

(73) Assignee: THE UNIVERSITY OF CHICAGO, Chicago, IL (US)

( * ) Notice: Subject to any disclaimer, the term of this patent is extended or adjusted under 35 U.S.C. 154(b) by 320 days.

(21) Appl. No.: 16/649,919

(22) PCT Filed: Oct. 23, 2018

(86) PCT No.: PCT/US2018/057004
§ 371 (c)(1),
(2) Date: Mar. 23, 2020

(87) PCT Pub. No.: WO2019/083934
PCT Pub. Date: May 2, 2019

(65) Prior Publication Data
US 2020/0305757 A1 Oct. 1, 2020

Related U.S. Application Data

(60) Provisional application No. 62/576,446, filed on Oct. 24, 2017.

(51) Int. Cl.
*A61B 5/055* (2006.01)
*G01R 33/48* (2006.01)
(Continued)

(52) U.S. Cl.
CPC .......... *A61B 5/055* (2013.01); *G01R 33/4824* (2013.01); *G01R 33/4835* (2013.01); *G01R 33/56316* (2013.01); *G01R 33/56325* (2013.01)

(58) Field of Classification Search
CPC ............ G01R 33/4824; G01R 33/4835; G01R 33/56316; G01R 33/56325
See application file for complete search history.

(56) References Cited

U.S. PATENT DOCUMENTS 8,958,866 B2    2/2015  Bolar et al.
2008/0315877 A1  12/2008  Osman
(Continued)

OTHER PUBLICATIONS

The International Search Report and Written Opinion issued for International Patent Application No. PCT/US18/57004 dated Jan. 11, 2019; pp. 1-8.

(Continued)

*Primary Examiner* — Gregory H Curran
(74) *Attorney, Agent, or Firm* — Bell & Manning, LLC

(57) ABSTRACT

An apparatus to jointly measure oxygen utilization and tissue strain includes an imaging system and a computer processor operatively coupled to the imaging system. The computer processor is configured to control the imaging system to perform a pulse sequence on tissue of a subject. The computer processor also acquires oxygen utilization data and strain data responsive to the pulse sequence. The computer processor further determines an amount of strain on the tissue of the subject based at least in part on the strain data and an amount of oxygen utilization of the tissue of the subject based at least in part on the oxygen utilization data.

20 Claims, 6 Drawing Sheets

(51) Int. Cl.
    *G01R 33/483*     (2006.01)
    *G01R 33/563*     (2006.01)

(56) References Cited

U.S. PATENT DOCUMENTS

| | | |
|---|---|---|
| 2010/0282258 A1 | 11/2010 | Tailor et al. |
| 2012/0062227 A1 | 3/2012 | Stuber et al. |
| 2017/0311839 A1* | 11/2017 | Osman ............... A61B 5/7207 |
| 2018/0271375 A1* | 9/2018 | Dharmakumar ..... G01R 33/481 |
| 2019/0117073 A1* | 4/2019 | Jolly .................... G06T 7/12 |

OTHER PUBLICATIONS

Subramanian et al., "Evaluation of Partial k-space strategies to speed up Time-domain EPR Imaging," In: *Magn Reson Med*. Sep. 2013, vol. 70, No. 3, pp. 745-753.

* cited by examiner

FIG. 2

|  | Slice Number Order | | | | |
|---|---|---|---|---|---|
| mOU(1): BH #1 | 1 | 2 | 3 | 4 | 5 |
| mOU(2): BH #2 | 2 | 3 | 4 | 5 | 1 |
| mOU(3): BH #3 | 3 | 4 | 5 | 1 | 2 |
| mOU(4): BH #4 | 4 | 5 | 1 | 2 | 3 |
| mOU(5): BH #5 | 5 | 1 | 2 | 3 | 4 | ns
COMBINED OXYGEN UTILIZATION, STRAIN, AND ANATOMIC IMAGING WITH MAGNETIC RESONANCE IMAGING

CROSS-REFERENCE TO RELATED APPLICATION

The present application is a national stage application which claims the priority benefit of International Patent App. No. PCT/US2018/057004 filed on Oct. 23, 2018, which claims the priority benefit of U.S. Provisional Patent Application No. 62/576,446 filed on Oct. 24, 2017, the entire disclosures of which are incorporated by reference herein.

BACKGROUND

The BOLD (i.e., blood oxygen level dependent) effect is caused by the magnetic differences between diamagnetic oxygenated hemoglobin ("oHb") and paramagnetic deoxygenated hemoglobin ("dHb"). Changes in the amount of dHb in the blood cause linear local susceptibility shifts, and changes in the ratio of oHb and dHb can be derived by measuring these frequency shifts. The BOLD effect can be utilized in techniques for cardiac imaging. However, BOLD contrast exhibits a low (e.g., about 15 percent) difference in signal intensity between hemodynamically stable and unstable regions. Cardiac magnetic resonance imaging ("MRI") techniques that are based on the BOLD effect rely on relative regional differences, and will therefore be less reliable for assessing globally reduced diseased tissue states, such as diffused fibrosis. Moreover, cardiac MRI techniques that are based on the BOLD effect are susceptible to both acquisition imperfections and motion artifacts that further reduce sensitivity.

SUMMARY

An illustrative apparatus to jointly measure oxygen utilization and tissue strain includes an imaging system and a computer processor operatively coupled to the imaging system. The computer processor is configured to control the imaging system to perform a pulse sequence on tissue of a subject. The computer processor also acquires oxygen utilization data and strain data responsive to the pulse sequence. The computer processor further determines an amount of strain on the tissue of the subject based at least in part on the strain data and an amount of oxygen utilization of the tissue of the subject based at least in part on the oxygen utilization data.

An illustrative method of jointly measuring oxygen utilization and tissue strain includes controlling, by a computer processor, an imaging system to perform a pulse sequence on tissue of a subject. The method also includes acquiring, by the computer processor, oxygen utilization data and strain data responsive to the pulse sequence. The method further includes determining, by the computer processor, an amount of strain on the tissue of the subject based at least in part on the strain data and an amount of oxygen utilization of the of tissue of the subject based at least in part on the oxygen utilization data.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

FIG. 2 depicts an example slice ordering that can be used for oxygen utilization segments in successive repetitions of a pulse sequence in accordance with an illustrative embodiment.

DETAILED DESCRIPTION

Figure 1:
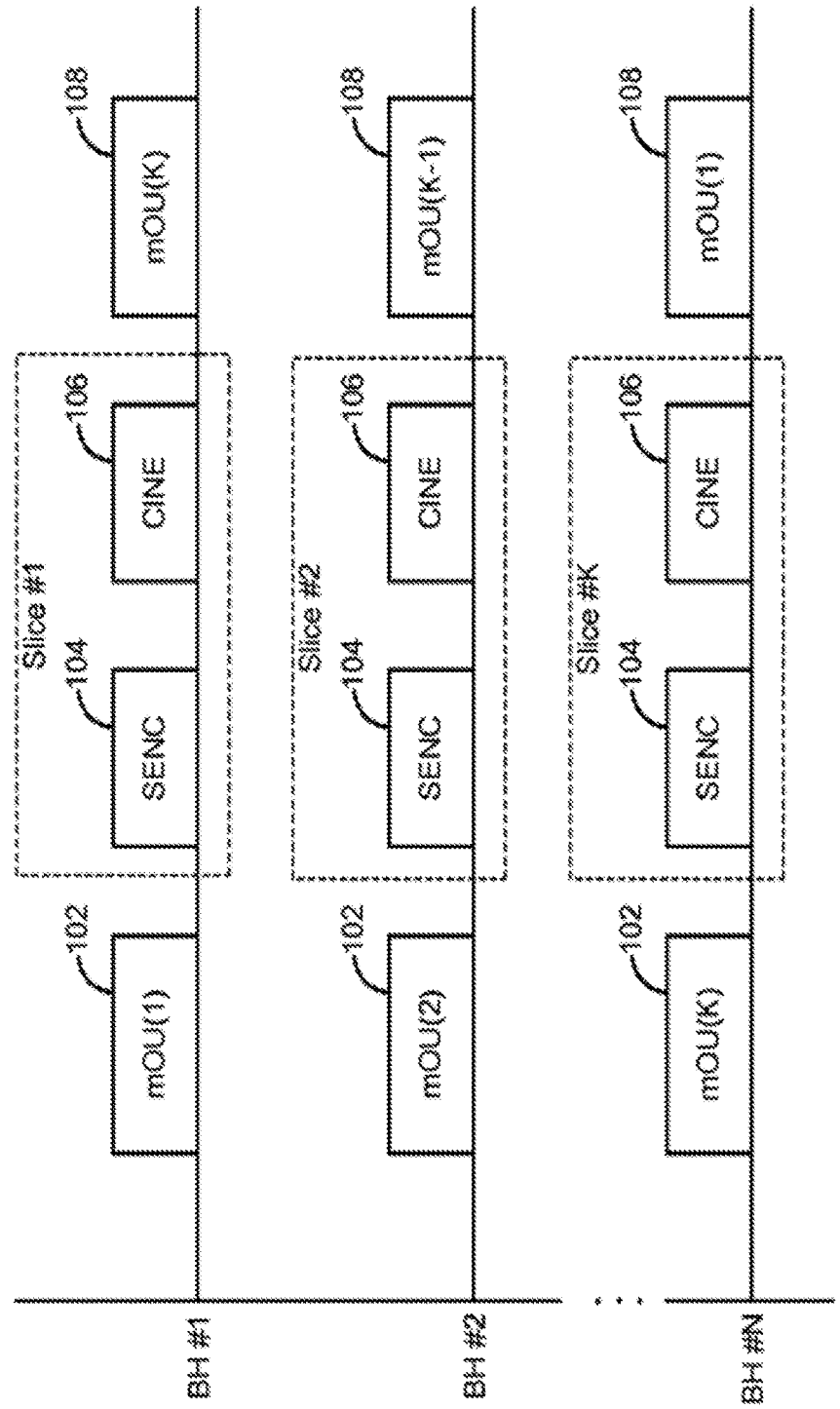
FIG. 1 is a block diagram depicting a pulse sequence that includes oxygen utilization imaging segments, a strain imaging segment, and an anatomic imaging segment in each repetition in accordance with an illustrative embodiment.

Use of the BOLD effect in MRI imaging has several limitations, including a lack of reliability for assessing globally reduced diseased tissue states, and insufficient sensitivity due to acquisition imperfections and motion artifacts. Research efforts to overcome these challenges include imaging at higher field strengths (e.g., 3 Tesla (T)) for increased signal strength, dedicated post-processing for diseased tissue segmentation, and using consecutively repeated acquisitions over 5-10 minute periods. Most recently, exploitation of freely obtained k-space phase information has been proposed to shift the BOLD sensitivity limitation due to assessing magnitude images alone.

Over the past decade, quantitative susceptibility mapping ("QSM"), which is a hybrid acquisition and reconstruction approach, has become well-established for the quantification of susceptibility in the brain and other vasculature. The pulse sequence acquisitions for both BOLD and QSM are similar, in that they both implement a multi-echo sampling scheme. A key difference between these two approaches is as follows: while BOLD assumes no geometric susceptibility-induced relationships between adjacent voxels, QSM formulates the precise relationship between adjacent tissues due to the main magnetic field. In QSM, several dedicated post-processing operations are used to mathematically solve a non-linear inversion problem and derive the quantitative field map solution.

Two representative QSM schemes are a multi-orientation sampling strategy that multiplies the total scan time, and a regularized iterative method using convex optimization that employs magnitude-based a priori preconditioning. This latter technique, which can be referred to as Morphology-Enabled Dipole Inversion ("MEDI"), minimizes the number of edge voxels in the susceptibility map to be consistent with the magnitude image. There remains a need, however, for improved oxygen utilization measurements using MRI, especially for cardiac MRI applications where additional data such as strain and anatomical information are useful for characterizing cardiac tissue health.

The present disclosure addresses the aforementioned drawbacks in imaging by providing a method for jointly measuring oxygen utilization and strain with anatomic imaging using an MRI system. Data are acquired from a subject during a breath-hold period with an MRI system by controlling the MRI system to perform a pulse sequence that includes acquiring oxygen utilization data, strain data, and anatomic image data in each repetition of the pulse sequence. In an illustrative embodiment, an image depicting anatomy of the subject is reconstructed from the anatomic image data, and a strain map having pixel values associated with strain in the anatomy of the subject is generated from the strain data. Additionally, an oxygen extraction fraction map having pixel values associated with oxygen extraction fraction in the anatomy of the subject is generated from the oxygen utilization data.

More specifically, described here are systems and methods for computing quantitative measurements of oxygen utilization of the heart muscle (e.g., myocardium) using magnetic resonance imaging and a data acquisition scheme in which oxygen utilization data are acquired together with strain data and anatomic image data in a single scan. To this end, a multi-parametric biomarker approach of acquiring strain and oxygen utilization data in the heart with a joint anatomy acquisition (e.g., cine MRI) without contrast agent is described. With this acquisition scheme, a motion-invariant mathematical transformation of the dynamically moving heart using reference dynamic measurements of cardiac motion can also be acquired in the same scan. The quantitative parameters extracted using the methods described in the present disclosure can provide information about oxygen content in tissues.

It is known that changes in myocardial oxygen utilization ("mOU") precede tissue cell death (e.g., infarction) in patients predisposed to heart attack and in patients suffering from rejection of a transplanted heart (e.g., cardiac allograft vasculopathy). The systems and methods described in the present disclosure provide a technique for measuring oxygen utilization that is highly sensitive to small physiologic changes in the heart. In general, the techniques described in the present disclosure include a data acquisition operation, an algorithmic processing operation to extract a physiologic signal, and an operation of producing and displaying an image or quantitative output.

As discussed in detail below, the methods described in the present disclosure provide a simultaneous, single-scan approach for acquiring anatomy, mOU, and strain data. Quantitative oxygen utilization can be determined by measuring transient susceptibility changes within an inter-beat (R-R) interval. The mOU data are acquired in the same scan as a simultaneous strain and anatomic imaging (e.g., a SENC+Cine) acquisition. Strain imaging, such as Strain-Encoded (SENC) imaging, can quantify subtle dysfunctions in myocardial strain that precede the development of bulk regional wall motion abnormalities. Using the techniques described herein, a combined strain and anatomic imaging (e.g., SENC+Cine) scan in a single breath-hold can be used to derive myocardium position, and can eliminate inter-sequence motion error between strain and anatomic imaging.

FIG. 1 is a block diagram depicting a pulse sequence that includes oxygen utilization imaging segments, a strain imaging segment, and an anatomic imaging segment in each repetition in accordance with an illustrative embodiment. The pulse sequence acquires three different data types within a single scan, which may be performed in a single breath-hold period. The data acquired with the pulse sequence include data corresponding to anatomic images, data corresponding to strain images, and data corresponding to oxygen utilization, such as myocardial oxygen utilization.

In general, the pulse sequence includes a first myocardial oxygen utilization ("mOU") imaging segment 102, a strain imaging segment 104, an anatomical imaging segment 106, and a second mOU imaging segment 108. In alternative embodiments, the pulse segment may include fewer, additional, and/or different segments. The pulse sequence may be performed once per breath-hold ("BH") period during which the subject being imaged holds his/her breath. In an illustrative embodiment, the pulse sequence is repeated to acquire data from different slice locations within the subject. It will be appreciated that the order of the first mOU imaging segment 102, the strain imaging segment 104, the anatomic imaging segment 106, and the second mOU imaging segment 108 can be different from that shown in FIG. 1. That is, different permutations of the pulse sequence segments are contemplated and can be implemented as desired.

In each repetition of the pulse sequence, multiple slices are imaged in both the first mOU imaging segment 102 and the second mOU imaging segment 108. The number of slices used can be 2, 4, 5, 8, 10, etc. For instance, each slice can be imaged in both the first mOU imaging segment 102 and the second mOU imaging segment 108.

In an illustrative embodiment, the order in which the slices are imaged in the first mOU imaging segment 102 and the second mOU imaging segment 108 is different in each repetition of the pulse sequence. For example, a different permutation of slice ordering can be used in each mOU imaging segment in each different repetition of the pulse sequence.

FIG. 2 depicts an example slice ordering that can be used for oxygen utilization segments in successive repetitions of a pulse sequence in accordance with an illustrative embodiment. In FIG. 2, there are five different slice locations and the slice order indexing is designed in such a manner to facilitate mOU signal evolution within each breath-hold scan. For example, as shown in FIG. 1, the first mOU imaging segment can use the slice order permutations in ascending order (e.g., 1, 2, . . . , K for K total slices and corresponding slice order permutations) across N total breath-hold periods, and the second mOU imaging segment can use the slice order permutations in descending order (e.g., K, K−1, . . . , K). In alternative embodiments, different slice order permutations may be used. In many instances the total number of breath-hold periods will equal the total number of slices (i.e., N=K). It will be appreciated that slice order combinations other than those described here can also be used depending on the total number of slices and breath-hold periods. For instance, the slice order permutations do not need to be used in an ascending or descending order, but instead may be randomly selected for each successive breath-hold period. Alternatively, a mathematical formula may be used to determine slice order permutations. As shown in FIG. 1, the mOU imaging segments bookend the beginning and end of each breath-hold, which can advantageously overcome cross-talk interferences in the case of a fully same-slice acquisition.

Although multiple slices are imaged in the first mOU imaging segment 102 and the second mOU imaging segment 108 in each repetition of the pulse sequence, only one slice is typically imaged during the strain imaging segment 104 and the anatomical imaging segment 106 of each repetition of the pulse sequence. In general, the same slice is imaged during the strain imaging segment 104 and the anatomical imaging segment 106 in a given repetition of the pulse sequence. It will be appreciated, however, that multiple slices can also be imaged in one or both of the strain imaging segment 104 and anatomic imaging segment 106 in each repetition of the pulse sequence. For example, simultaneous multi-slice imaging techniques may be implemented to provide multislice imaging without significant loss in temporal resolution, or significant increase in overall scan time.

The pulse sequence can be preceded by a prescan, in which prescan data is acquired. The prescan data can be acquired for all slices, and can include combined prescan data for the mOU, strain, and anatomical imaging segments. As an example, the prescan data can include data used to calibrate echoes for the purposes of calibrating k-space trajectories to improve image quality. The prescan data can also include chemical based (i.e., spectral) shift data from a target region and/or parameters associated with minimization of field inhomogeneity such as shim, orientation-specific gradient hardware calibrations, etc.

One example of a strain imaging segment includes a strain encoding ("SENC") MRI segment. The anatomic imaging sequence preferably includes a cine data acquisition technique, such as a balanced steady-state free precession (bSSFP) technique or other suitable cine cardiac MRI technique.

Figure 3:
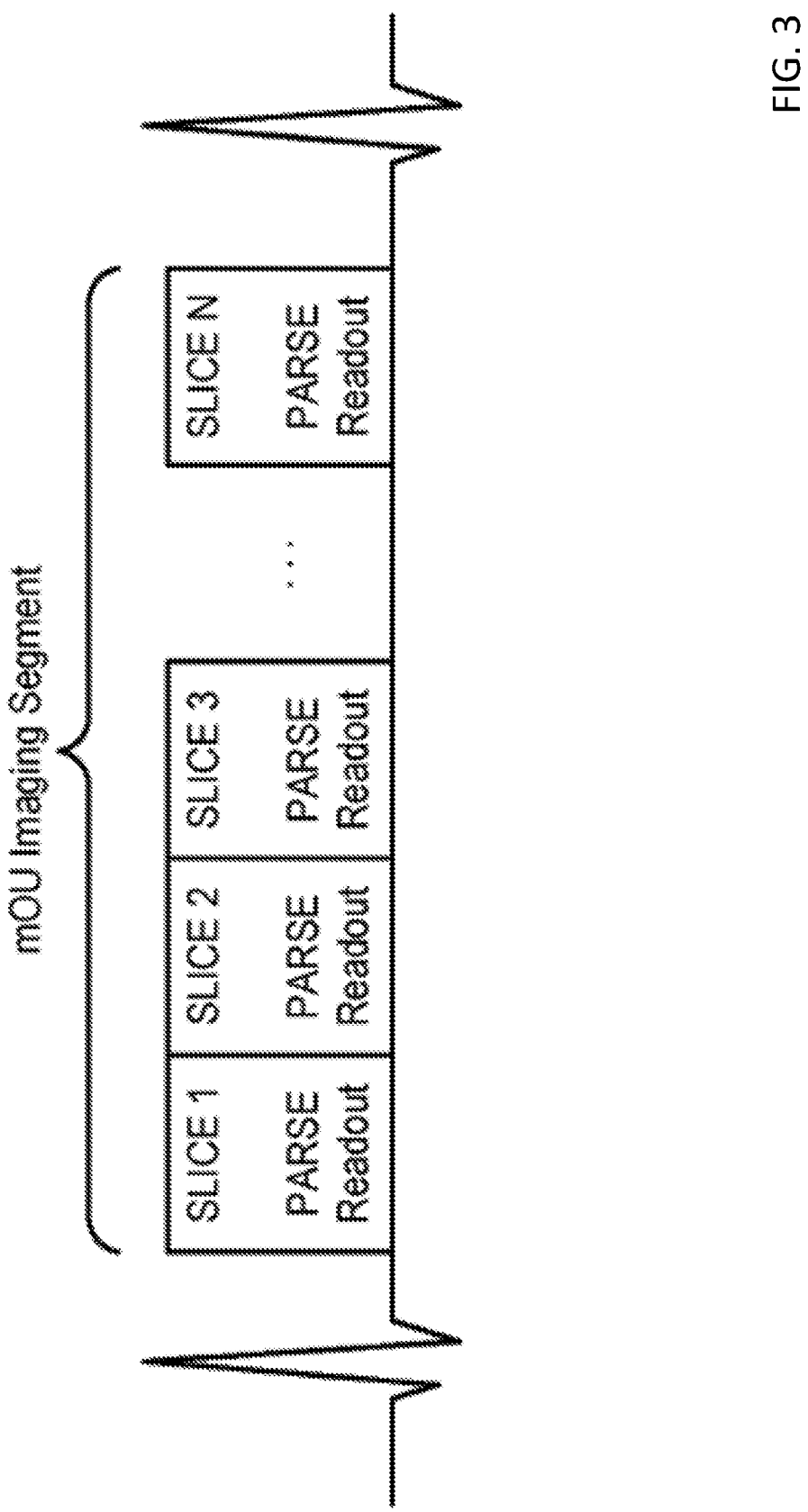
FIG. 3 depicts an example of an mOU imaging segment implemented in a pulse sequence in accordance with an illustrative embodiment.

FIG. 3 depicts an example of an mOU imaging segment implemented in a pulse sequence in accordance with an illustrative embodiment. The mOU imaging segment can include a multislice, cardiac-gated mOU sequence with fat suppression and high spatial resolution (e.g., 1 mm$^2$). In alternative embodiments, a different spatial resolution may be used such as a spatial resolution between ~0.05 mm$^2$ and ~3-4 mm$^2$. Also, a single number map may include an aggregate average across the entire image, which is equivalent to a centimeter scale resolution. As one example, a multislice Parameter Assessment by Retrieval from Signal Encoding (PARSE) acquisition can be implemented to acquire mOU data across different phases of the cardiac cycle. In alternative embodiments, a Medical Imaging Quantitative Susceptibility Mapping (MEDI-QSM) acquisition can be used for the mOU imaging segments.

As shown in FIG. 1, the mOU data are collected during the first and last heart beats of each repetition of the pulse sequence. In the multislice PARSE acquisition, a spatial-spectral (SPSP) water-selective radio frequency (RF) excitation pulse is used to satisfy PARSE-PLCG's single Lorentzian water peak (0 Hz) model assumption.

Figure 4:
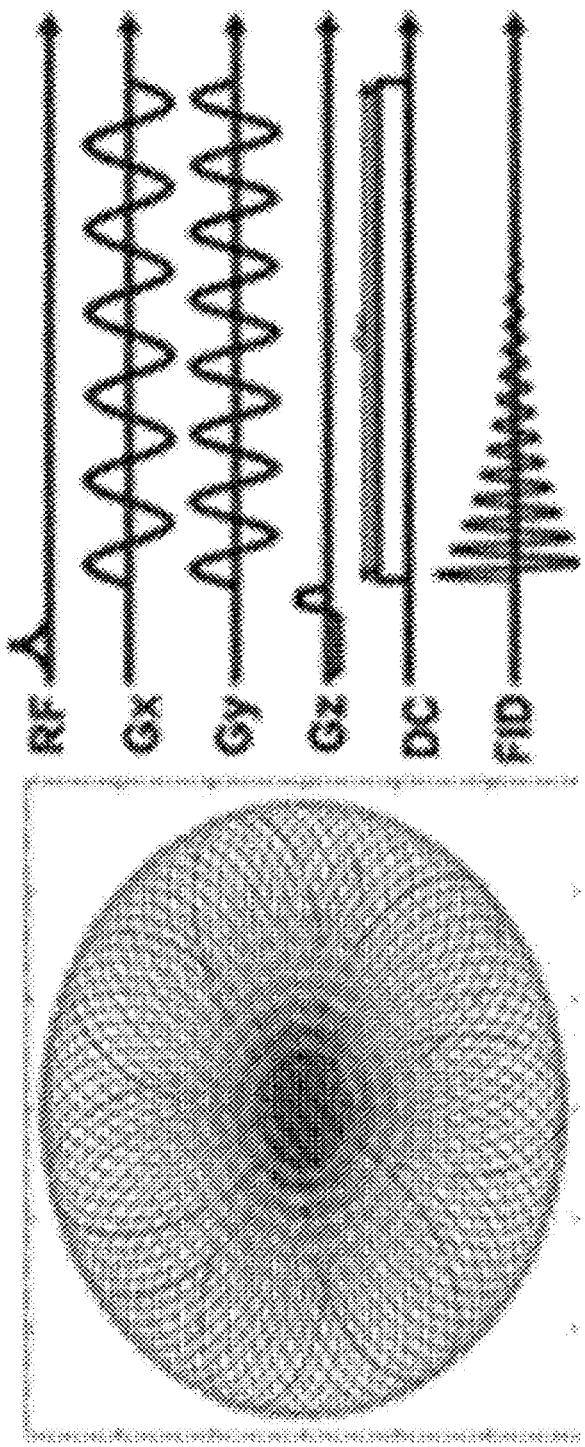
FIG. 4 is an example of a Rosette sampling trajectory and corresponding pulse sequence segment in accordance with an illustrative embodiment.

In another illustrative embodiment, the mOU data can be acquired by sampling k-space using three sets of Rosette interleaves. FIG. 4 is an example of a Rosette sampling trajectory and corresponding pulse sequence segment in accordance with an illustrative embodiment. As one example, three sets of Rosette interleaves can be acquired at 24 millisecond (ms) or 48 ms readouts using a sliding window to achieve 1 mm$^2$ in-plane spatial resolution and (24×3)−(48×3)=72-144 temporal resolution. In alternative embodiments, a different spatial resolution and/or range of temporal resolutions may be used. With a single-leaf sampling pattern, the central k-space employed for effective image reconstruction in the presence of notable water-air interface may be limited. Thus, the tri-leaf sampling pattern triples the number of free induction decay (FID) signals with the Rosette k-space sampled 120 degrees apart.

Figure 5:
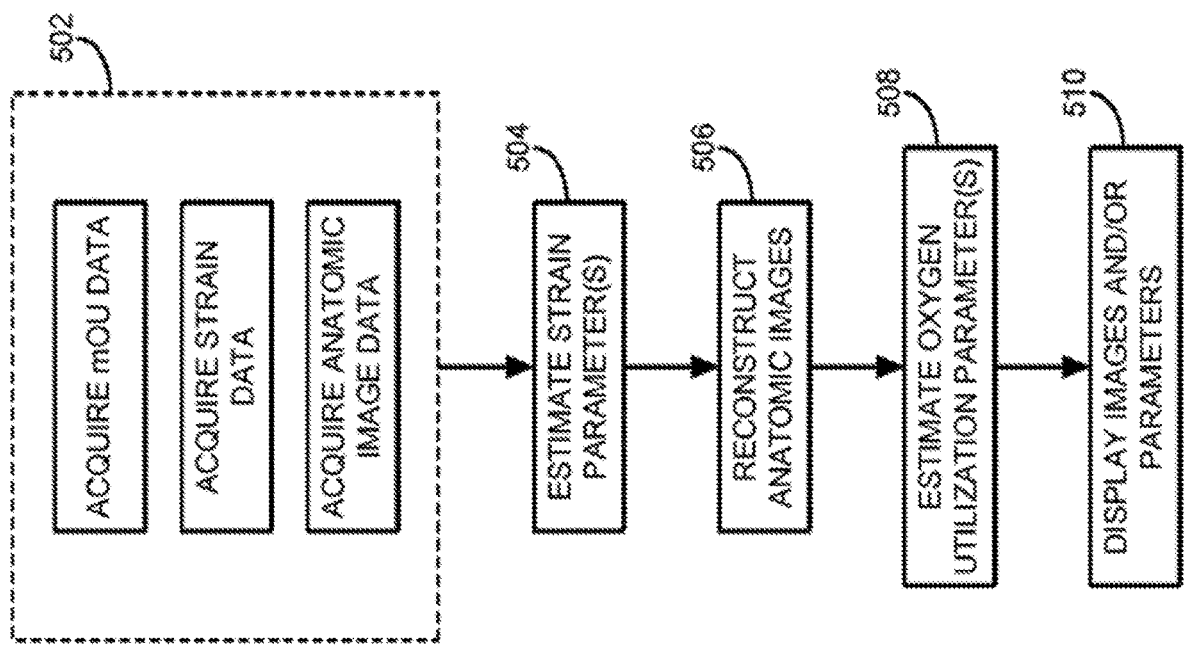
FIG. 5 is a flow diagram depicting operations of an example method for assessing myocardial tissue using a pulse sequence in accordance with an illustrative embodiment.

FIG. 5 is a flow diagram depicting operations of an example method for assessing myocardial tissue using a pulse sequence in accordance with an illustrative embodiment. In the example of FIG. 5, multiple different types of data are acquired in each repetition of the pulse sequence. More specifically, FIG. 5 depicts a process for jointly acquiring oxygen utilization, strain, and anatomic imaging data in a single scan and producing images based on the acquired data.

In an operation 502, data is acquired from a subject using an MRI system. Any type of MRI system known in the art may be used. The data acquisition operation 502 includes performing multiple repetitions of a pulse sequence that includes, in each repetition, a first mOU imaging segment, a strain imaging segment, an anatomical imaging segment, and a second mOU imaging segment. The acquired data thus includes mOU data, strain data, and anatomical image data. In one embodiment, an anatomic image, a frequency shift, and a relaxometry map can be mathematically combined to yield a percentage value of oxygenation. Alternatively, the oxygenation can be converted to parts per million (ppm) based on the percentage. With respect to strain data, raw data is linearly correlated to the extent of mechanical tension (i.e., positive) or compression (i.e., negative). Specifically, a linear mathematical operation allows for conversion from raw measurements centered at an operator specified frame of reference to a percentage value that maps to tension or compression as a percentage. Preferably, each repetition of the pulse sequence is performed in a different breath-hold period, as described above. In some implementations, the data acquisition operation is preceded by the acquisition of prescan data, as described above. In some other implementations, previously acquired prescan data can be provided, such as by retrieving prescan data from a memory or other data storage. In another embodiment, prescan data may not be used.

In an operation 504, a strain parameter is estimated based on the strain data. In one embodiment, SENC processing can be used to estimate strain in the myocardial tissue. The strain parameter can be a percentage value derived from displacement measures obtained within the image (tagging, SENC, feature tracking, etc.). In an illustrative embodiment, any type of strain parameter and/or strain parameter estimation process can be used.

In an operation 506, one or more images that depict the subject's anatomy are reconstructed based on the anatomic image data acquired in the operation 502. Any standard or customized reconstruction approach may be used.

In an operation 508, an oxygen utilization parameter is estimated based on the acquired mOU data from the operation 502. For example, an oxygen extraction fraction ("OEF") parameter can be estimated from the mOU data. The OEF, or other oxygen utilization parameter, can be estimated as a percentage for spatial locations in each slice, such that an OEF map that depicts the spatial distribution of OEF in a given slice can be produced. The OEF can also be calculated in ppm or other unit.

The OEF parameter can be estimated based on an estimation of frequency shifts, $\delta\omega$, induced by deoxyhemoglobin, and which are encoded in the mOU data. To estimate frequency shifts, it is known that the raw signal contains a combination of the target frequency at all positions. A standard convex optimization algorithm can be used to iteratively estimate what these values are by examining a segment of the data, its corresponding coordinates, and associated anatomy and R2 measures simultaneously towards an improved estimate. In alternative embodiments, any other process may be used to estimate frequency shifts. In an illustrative embodiment, the following relationship can be used to relate these frequency shifts to OEF:

$$\delta\omega = \gamma \cdot \frac{4}{3} \cdot \pi \cdot \Delta\chi_0 \cdot Hct \cdot OEF \cdot B_0, \qquad \text{Eq. 1}$$

where $\Delta\chi_0$ is the susceptibility difference between oxygenated and deoxygenated blood, Hct is the hematocrit, and $B_0$ is the magnetic field strength in Tesla. To estimate OEF, the local frequency is estimated in each pixel to generate local frequency maps. These frequency maps are quantitative maps of the local off-resonance frequency $\delta\omega$ and thus can be used to estimate the OEF.

The PARSE method can be used to simultaneously estimate $M_0$, $R^*_2$, and $\delta\omega$, from which OEF can be estimated. For instance, for each cardiac phase, the mOU data (e.g., the tri-leaf k-space Rosettes) can be processed using a PARSE-OEF reconstruction with a joint $M_0$, $R^*_2$, and frequency map estimation using a progressively linear conjugate gradient (PLCG) iteration. Alternatively, a different numerical approach can be used. Manual, semi-automatic, or automatic segmentation of the left ventricular ("LV") and right ventricular ("RV") myocardium can be used to weigh the contributions from these voxels for CG descent. In some implementations, segmentation of the LV and RV myocardium can proceed on a semi-automatic or automatic basis using the strain data and anatomic image data. For instance, the strain measured at end-systolic phase can identify the moving myocardium and, using this information, LV segmentation can be performed.

After deriving the frequency maps across each cardiac phase, an independent component analysis (ICA) or other suitable processing technique can be used to extract transient susceptibility changes throughout the cardiac cycle. The reconstructed images and estimated parameters or parameter maps are displayed or otherwise provided to a user in an operation 510. For example, the images, maps, and parameters can be displayed on a computer display or screen of a computing device. The data can also be stored in a memory or database, published to a website, transmitted to remote devices, etc. such that an end user is able to access and use the data. It is noted that although operations 504-508 of FIG. 5 are shown as separate operations, it will be appreciated that joint estimation techniques can be implemented to jointly estimate anatomic images and quantitative parameters (e.g., strain, OEF, etc.).

One implementation of the proposed techniques is a clinical assessment and visualization method and apparatus. In such an implementation, quantitative measures can be displayed over a reference two dimensional (2D) anatomical image, a 2D slice projection from a three dimensional (3D) reference volume, a 2D temporal snapshot in a dynamic image reference (e.g., animation with temporal frames), a 2D projection of a 3D dynamic volume, etc. These displays can be provided using an intuitive and easy-to-use interactive interface for the user.

In one embodiment, the system provides simultaneous display of two or more different measurements (e.g., measurement #1 and measurement #2) and reference anatomical coordinates. As one example, a simple colormap overlay of target measurement #1 can be provided over measurement #2, which can contain morphological information, while a user interaction (e.g., a dragging action using a mouse) provides custom toggling of a region-of-interest ("ROI") to a tailored region of anatomy to thereby allow assessment of both measurements #1 and #2 in a joint manner. Here, measurements #1 and #2 can be selected from the mOU data, strain data, anatomic image data, or parameters, parameter maps, or images generated from such data.

In some embodiments, cardiac motion in the mOU data can be addressed by using a bulls-eye-space transformation of the myocardium derived from fused regions of the strain and anatomic images. An a priori position of myocardium can be derived from fused SENC anatomy and/or strain maps with a cine MRI reference image, and the moving LV myocardium can be segmented using feature tracking.

In some other embodiments, to address the technical challenges associated with automated feature-tracking for cardiac MRI, high-frame-rate cine MRI techniques can be implemented. A mathematical transformation of the segmented LV myocardium into a bulls-eye model can then be performed, on which the ICA-based OEF extraction can be performed. This image space-to-bulls-eye space transformation is a linear mathematical operation and is therefore invertible (i.e., the bulls-eye space images and data can be transformed back to any phase of the cardiac cycle, and the transient mOU changes across the R-R interval can be shown on the myocardium).

In some implementations, the mOU post-processing can include reformulating the direct $R^*_2$ and frequency estimation process using the simultaneously acquired strain and anatomic image data. For instance, in the processing described above, pixel-wise three-parameter estimation is formulated to solve for anatomy ($M_0$), frequency (for deriving mOU), and $R^*_2$ in a simultaneous manner. The PLCG approach is a convex global minimization that includes of a set of linear and mostly unitary mathematical operators. A two-parameter estimation that employs simultaneously acquired anatomic images for the $M_0$ prior can be used to yield computationally faster convergence.

In some other implementations, a regularized $\delta\omega$ estimation in strain and anatomic image-derived myocardial tissue can be used. In these instances, an inverse-approach to the k-space/image space post-processing described above for the PARSE-PLCG algorithm can be used. The myocardial region is first identified from the fused strain and anatomic reference image. A pixel-wise joint $R^*_2$ and frequency map estimation is then selectively performed from the rosette FID k-space and corresponding k-space coordinates. Instead of a linear progression along the sampled rosette over the $R^*_2$ decay, iterations can be performed from a lower spatial resolution to more finely divided voxels. In this spatial resolution descent approach, the frequency and $R^*_2$ estimations can first be derived with conservative and large voxels, and then gradually improved to smaller voxel estimations over subsequent iteration steps.

Figure 6:
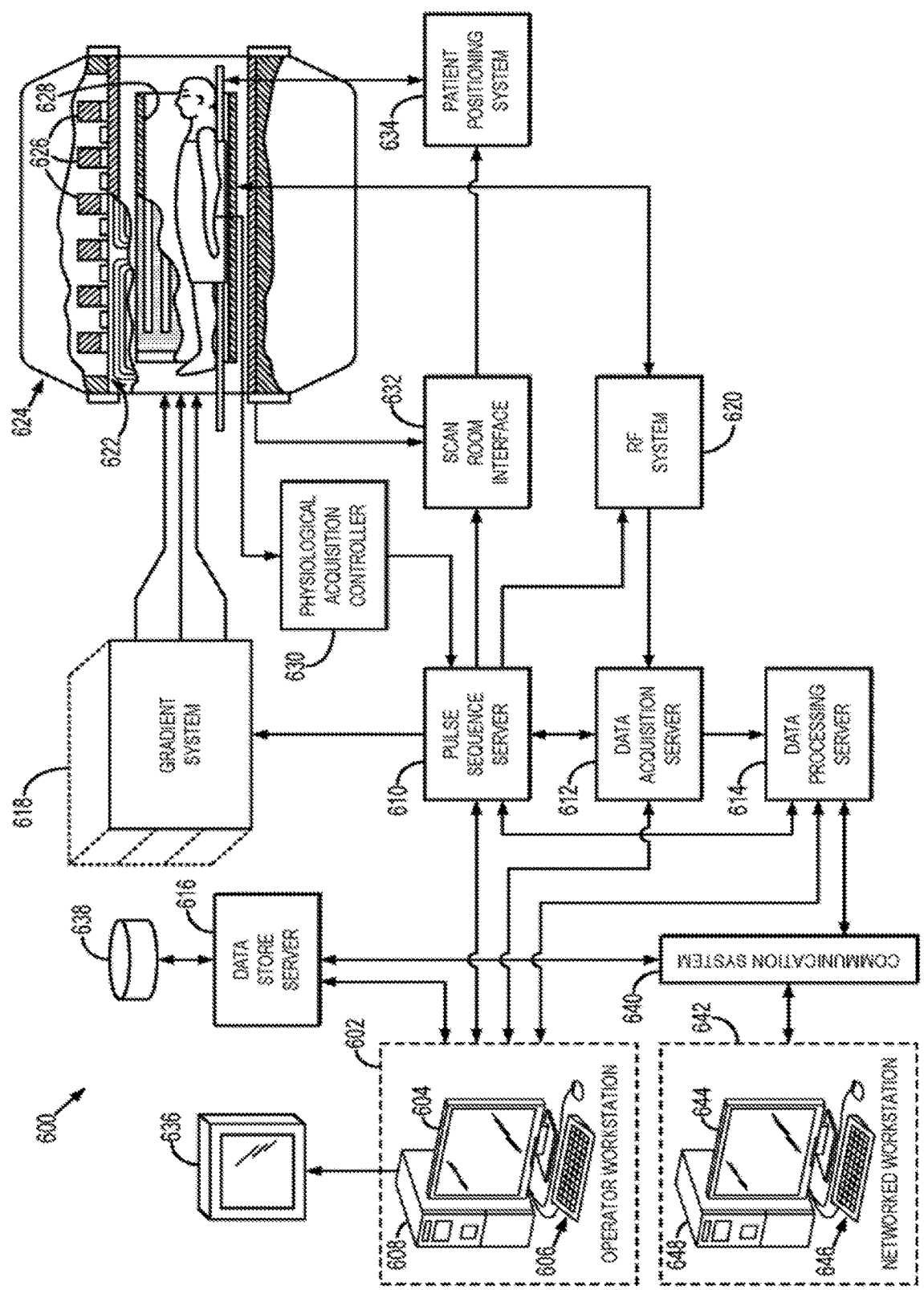
FIG. 6 is a block diagram of an example MRI system to implement the methods described herein in accordance with an illustrative embodiment.

FIG. 6 depicts an MRI system 600 to implement the methods described herein in accordance with an illustrative embodiment. The MRI system 600 includes an operator workstation 602 that may include a display 604, one or more input devices 606 (e.g., a keyboard, a mouse), a processor 608, and other computing components such as a transceiver, a memory, ports, buses, etc. The processor 608 may include a commercially available programmable machine running a commercially available operating system. The operator workstation 602 provides an operator interface that facilitates entering scan parameters into the MRI system 600. The operator workstation 602 may be coupled to different servers, including, for example, a pulse sequence server 610, a data acquisition server 612, a data processing server 614, and a data store server 616. The operator workstation 602 and the servers 610, 612, 614, and 616 may be connected via a communication system 640, which may include wired or wireless network connections.

The pulse sequence server 610 functions in response to instructions provided by the operator workstation 602 to operate a gradient system 618 and a radiofrequency ("RF") system 620. Gradient waveforms for performing a prescribed scan are produced and applied to the gradient system 618, which then excites gradient coils in an assembly 622 to produce the magnetic field gradients $G_x$, $G_y$, and $G_z$ that are used for spatially encoding magnetic resonance signals. The gradient coil assembly 622 forms part of a magnet assembly 624 that includes a polarizing magnet 626 and a whole-body RF coil 628.

RF waveforms are applied by the RF system 620 to the RF coil 628, or a separate local coil to perform the prescribed magnetic resonance pulse sequence. Magnetic resonance signals that are responsive to the pulse sequence are detected by the RF coil 628, or a separate local coil, and are thus received by the RF system 620. The responsive magnetic resonance signals may be amplified, demodulated, filtered, and/or digitized under direction of commands produced by the pulse sequence server 610. The RF system 620 includes an RF transmitter for producing a wide variety of RF pulses used in MRI pulse sequences. The RF transmitter is responsive to the prescribed scan and direction from the pulse sequence server 610 to produce RF pulses of the desired frequency, phase, and pulse amplitude waveform. The generated RF pulses may be applied to the whole-body RF coil 628 or to one or more local coils or coil arrays.

The RF system 620 also includes one or more RF receiver channels. An RF receiver channel includes an RF preamplifier that amplifies the magnetic resonance signal received by the coil 628 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M = \sqrt{I^2 + Q^2},\qquad \text{Eq. 2}$$

and the phase of the received magnetic resonance signal may also be determined according to the following relationship:

$$\varphi = \tan^{-1}\left(\frac{Q}{I}\right).\qquad \text{Eq. 3}$$

The pulse sequence server 610 can receive patient data from a physiological acquisition controller 630. By way of example, the physiological acquisition controller 630 may receive signals from a number of different sensors connected to the patient, including electrocardiograph ("ECG") signals from electrodes, or respiratory signals from a respiratory bellows or other respiratory monitoring devices. These signals may be used by the pulse sequence server 610 to synchronize, or "gate," the performance of the scan with the subject's heart beat or respiration.

The pulse sequence server 610 may also connect to a scan room interface circuit 632 that receives signals from various sensors associated with the condition of the patient and the magnet system. Through the scan room interface circuit 632, a patient positioning system 634 can receive commands to move the patient to desired positions during the scan.

The digitized magnetic resonance signal samples produced by the RF system 620 are received by the data acquisition server 612. The data acquisition server 612 operates in response to instructions downloaded from the operator workstation 602 to receive the real-time magnetic resonance data and provide buffer storage, so that data is not lost by data overrun. In some scans, the data acquisition server 612 passes the acquired magnetic resonance data to the data processor server 614. In scans that require information derived from acquired magnetic resonance data to control the further performance of the scan, the data acquisition server 612 may be programmed to produce such information and convey it to the pulse sequence server 610. For example, during pre-scans, magnetic resonance data may be acquired and used to calibrate the pulse sequence performed by the pulse sequence server 610. As another example, navigator signals may be acquired and used to adjust the operating parameters of the RF system 620 or the gradient system 618, or to control the view order in which k-space is sampled. In still another example, the data acquisition server 612 may also process magnetic resonance signals used to detect the arrival of a contrast agent in a magnetic resonance angiography (MRA) scan. For example, the data acquisition server 612 may acquire magnetic resonance data and process it in real-time to produce information that is used to control the scan.

The data processing server 614 receives magnetic resonance data from the data acquisition server 612 and processes the magnetic resonance data in accordance with instructions provided by the operator workstation 602. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 614 are conveyed back to the operator workstation 602 for storage. Real-time images may be stored in a data base memory cache, from which they may be output to operator display 602 or a display 636. Batch mode images or selected real time images may be stored in a host database on disc storage 638. When such images have been reconstructed and transferred to storage, the data processing server 614 can notify the data store server 616 on the operator workstation 602. The operator workstation 602 can be used by an operator to archive the images, produce films, send the images via a network to other facilities, etc.

The MRI system 600 also includes one or more networked workstations 642. For example, a networked workstation 642 may include a display 644, one or more input devices 646 (e.g., a keyboard, a mouse), a processor 648, and additional components such as a memory, transceiver, etc. The networked workstation 642 may be located within the same facility as the operator workstation 602, or in a different facility, such as a different healthcare institution or clinic.

The networked workstation 642 may gain remote access to the data processing server 614 or data store server 616 via the communication system 640. Accordingly, multiple networked workstations 642 may have access to the data processing server 614 and the data store server 616. In this manner, magnetic resonance data, reconstructed images, or other data may be exchanged between the data processing server 614 or the data store server 616 and the networked workstations 642, such that the data or images may be remotely processed by a networked workstation 642.

In an illustrative embodiment, any of the operations described herein can be implemented as computer-readable instructions which are stored on a computer-readable medium such as a computer memory. Upon execution by a processor the computer-readable instructions cause performance of the imaging operations described herein.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. An apparatus to jointly measure oxygen utilization and tissue strain, the apparatus comprising:
   an imaging system; and
   a computer processor operatively coupled to the imaging system, wherein the computer processor is configured to:
      control the imaging system to perform a pulse sequence on tissue of a subject;
      acquire oxygen utilization data responsive to the pulse sequence, wherein the pulse sequence includes a first oxygen utilization segment and a second oxygen utilization segment; and
      acquire strain data responsive to the pulse sequence, wherein the strain data is acquired in between the first oxygen utilization segment of the pulse sequence and the second oxygen utilization segment of the pulse sequence; and
      determine an amount of strain on the tissue of the subject based at least in part on the strain data and determine an amount of oxygen utilization of the tissue of the subject based at least in part on the oxygen utilization data.

2. The apparatus of claim 1, wherein the pulse sequence is performed during a breath-hold period during which the subject holds his or her breath.

3. The apparatus of claim 1, wherein the computer processor is also configured to acquire anatomic image data responsive to the pulse sequence.

4. The apparatus of claim 3, wherein the computer processor is configured to generate an oxygen extraction fraction map that has pixel values associated with oxygen utilization in the tissue of the subject.

5. The apparatus of claim 4, wherein the computer processor is configured to generate a strain map that has pixel values associated with strain in the tissue of the subject.

6. The apparatus of claim 1, wherein the oxygen utilization data includes first oxygen utilization data corresponding to the first oxygen utilization segment and second oxygen utilization data corresponding to the second oxygen utilization segment.

7. The apparatus of claim 6, wherein the pulse sequence includes a strain encoding (SENC) pulse segment, and wherein the strain data corresponds to the SENC pulse segment.

8. The apparatus of claim 7, wherein the pulse sequence includes a cine pulse segment, and wherein the processor acquires anatomic image data from the cine pulse segment.

9. The apparatus of claim 8, wherein the SENC pulse segment and the cine pulse segment occur in between the first oxygen utilization segment and the second oxygen utilization segment of the pulse sequence.

10. The apparatus of claim 8, wherein the first oxygen utilization data and the second oxygen utilization data are based on a plurality of slice locations in the tissue of the subject, and wherein the first oxygen utilization data is based on a first ordering of the plurality of slice locations and the second oxygen utilization data is based on a second ordering of the plurality of slice locations.

11. The apparatus of claim 1, wherein the computer processor is configured to control the imaging system to repetitively perform the pulse sequence, and wherein each repetition of the pulse sequence occurs during a breath-hold period of the subject.

12. The apparatus of claim 1, wherein the computer processor is configured to sample k-space using a Rosette trajectory to acquire the oxygen utilization data.

13. The apparatus of claim 1, wherein the computer processor is configured to determine frequency shifts caused by changes in deoxygenated hemoglobin levels in the subject, and wherein the oxygen utilization data is based at least in part on the frequency shifts.

14. A method of jointly measuring oxygen utilization and tissue strain, the method comprising:
   controlling, by a computer processor, an imaging system to perform a pulse sequence on tissue of a subject;
   acquiring, by the computer processor, oxygen utilization data during a first oxygen utilization segment of the pulse sequence and during a second oxygen utilization segment of the pulse sequence;
   acquiring strain data responsive to the pulse sequence, wherein the strain data is acquired in between the first oxygen utilization segment of the pulse sequence and the second oxygen utilization segment of the pulse sequence; and
   determining, by the computer processor, an amount of strain on the tissue of the subject based at least in part on the strain data and an amount of oxygen utilization of the of tissue of the subject based at least in part on the oxygen utilization data.

15. The method of claim 14, further comprising acquiring, by the computer processor, anatomic image data responsive to the pulse sequence.

16. The method of claim 14, further comprising generating, by the computer processor, an oxygen extraction fraction map based on the oxygen utilization data, wherein the oxygen extraction fraction map has pixel values associated with oxygen utilization in the tissue of the subject.

17. The method of claim 14, further comprising generating, by the computer processor and based on the strain data, a strain map that has pixel values associated with strain in the tissue of the subject.

18. The method of claim 14, wherein the oxygen utilization data includes first oxygen utilization data corresponding to the first oxygen utilization segment and second oxygen utilization data corresponding to the second oxygen utilization segment.

19. The method of claim 18, wherein the pulse sequence includes a strain encoding (SENC) pulse segment to obtain the strain data and a cine pulse segment to obtain anatomical image data, and wherein the SENC pulse segment and the cine pulse segment occur in between the first oxygen utilization segment and the second oxygen utilization segment of the pulse sequence.

20. The method of claim 18, wherein the first oxygen utilization data and the second oxygen utilization data are based on a plurality of slice locations in the tissue of the subject, and wherein the first oxygen utilization data is based on a first ordering of the plurality of slice locations and the second oxygen utilization data is based on a second ordering of the plurality of slice locations.

\* \* \* \* \*